United States Patent [19]
Nagura et al.

[11] Patent Number: 5,301,552
[45] Date of Patent: Apr. 12, 1994

[54] ULTRASONIC APPARATUS

[75] Inventors: Masato Nagura, Chofu; Toshiaki Takahashi, Tachikawa; Kazuhiko Hara, Yokohama, all of Japan

[73] Assignee: Canon Kabushiki Kaisha, Tokyo, Japan

[21] Appl. No.: 991,338

[22] Filed: Jan. 6, 1992

Related U.S. Application Data

[63] Continuation of Ser. No. 457,887, Dec. 27, 1989, abandoned.

[30] Foreign Application Priority Data

Jan. 20, 1989 [JP] Japan .................................. 1-12218

[51] Int. Cl.$^5$ ...................... G01N 29/10; G01N 29/26
[52] U.S. Cl. ......................................... 73/606; 73/629; 73/634
[58] Field of Search ................. 73/600, 606, 611, 627, 73/629, 634, 620

[56] References Cited

U.S. PATENT DOCUMENTS

| | | | |
|---|---|---|---|
| 3,934,458 | 1/1976 | Beretsky et al. | 73/67.9 |
| 4,173,897 | 11/1979 | Förstermann et al. | 73/611 |
| 4,563,898 | 1/1986 | Kanda et al. | 73/606 |
| 4,674,333 | 6/1987 | Jindo et al. | 73/606 |
| 4,730,494 | 3/1988 | Ishikawa et al. | 73/606 |
| 4,953,405 | 9/1990 | Hara et al. | |

FOREIGN PATENT DOCUMENTS

| | | | |
|---|---|---|---|
| 0072855 | 6/1980 | Japan | 73/629 |
| 0191543 | 11/1982 | Japan | 73/606 |
| 0191544 | 11/1982 | Japan | 73/606 |
| 0018755 | 1/1985 | Japan | 73/606 |
| 63-47658 | 2/1988 | Japan . | |
| 0118766 | 5/1989 | Japan | 73/627 |

*Primary Examiner*—Hezron E. Williams
*Assistant Examiner*—Rose M. Finley
*Attorney, Agent, or Firm*—Fitzpatrick, Cella, Harper & Scinto

[57] ABSTRACT

Ultrasonic apparatus that automatically adjusts the focus of ultrasonic waves to a desired depth within an object includes an ultrasonic probe which irradiates a focused ultrasonic beam onto an object to be inspected and a receiver which receives ultrasonic waves reflected from the object. A desired focusing depth is set and the inherent focal length of the probe and the velocity of sound within the object are detected to evaluate a distance between the probe and the object at which the focus of the probe coincides with the desired depth. The distance between the probe and the object is adjusted to coincide with the evaluated distance.

30 Claims, 2 Drawing Sheets

ULTRASONIC APPARATUS

This application is a continuation of application Ser. No. 07/457,887 filed Dec. 27, 1989, now abandoned.

BACKGROUND OF THE INVENTION

1. Field of the Invention

This invention relates to an ultrasonic apparatus provided with an autofocusing function.

2. Description of the Prior Art

Heretofore, in defect inspection of electronic components and the like by ultrasonic waves, one practical system uses a so-called pulse-echo method in which, for the purpose of increasing the resolution, ultrasonic pulses are emitted toward an object to be inspected in water using a focusing-type probe which focuses an ultrasonic beam into a narrow beam, and nondestructive inspection of the object is performed by analyzing signals reflected from the object. This method is described in detail in, for example, Japanese Patent Public Disclosure (Kokai) No. 63-47658 (1988).

In this method, the focus of the ultrasonic beam must exactly coincide with a desired depth to be inspected. The focal length of the probe is usually fixed, and focusing is performed by changing the distance between the probe and the object to be inspected. If the depth to be inspected within the object from the surface of the object is represented by d, the velocity of sound in water by $V_w$, the velocity of sound within the object to be inspected by $V_s$, and the focal length of the ultrasonic beam in water by F, then the target distance $W_p$ in water from the probe to the object to be inspected is expressed by $$W_p = F - d \cdot V_s / V_w.$$

Hence, it can be understood that the probe should be disposed at a position which is at a distance equal to the target distance $W_p$ in water from the surface of the object to be inspected.

In general, however, the velocity of sound $V_s$ within the object to be inspected is unknown, and the velocity of sound $V_w$ in water and the focal length F in water change mainly due to changes in water temperature. Moreover, there exists an inherent deviation from a nominal value in the focal length F in water for every probe.

Accordingly, in the conventional method, it is necessary to separately measure or estimate the above-described values before starting inspection. Furthermore, since there exists no means for automatically adjusting the position of the probe to the target length $W_p$ in water, the operator himself must perform any adjusting operation while measuring the distance in water. Consequently, this inspection method is troublesome, causes many misoperations, and is not an efficient method.

SUMMARY OF THE INVENTION

It is an object of the present invention to provide an ultrasonic apparatus capable of making the focus of an ultrasonic beam automatically coincide with a desired depth within an object to be inspected.

It is another object of the present invention to provide an ultrasonic inspection apparatus in which the focus of an ultrasonic beam can automatically be made to coincide with a desired depth to be inspected within an object to be inspected in order to perform the inspection of a plane to be inspected at the desired depth, and the result can be obtained as an ultrasonic image.

DETAILED DESCRIPTION OF THE PREFERRED EMBODIMENTS

Figure 1:
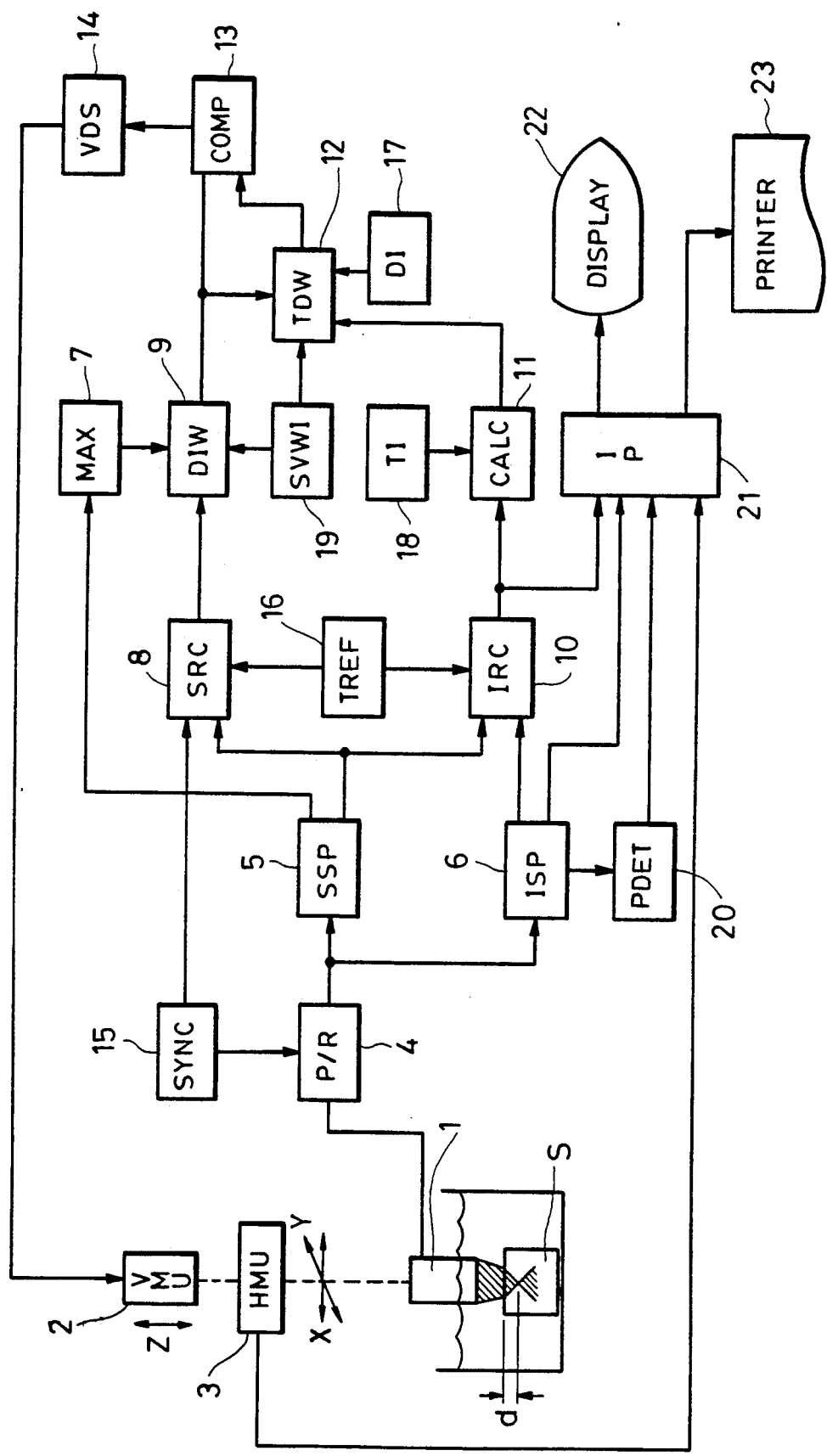
FIG. 1 is a block diagram of the circuit configuration of an ultrasonic apparatus according to a first embodiment of the present invention.

FIG. 1 shows a configurational block diagram of an ultrasonic measuring apparatus according to a first embodiment of the present invention. The apparatus of the present embodiment is used for inspection of electronic components, such as semiconductor-device packages, multilayer ceramic capacitors, high-density-mounted ceramic substrates and the like, performs nondestructive inspection of defects within an object to be inspected by ultrasonic wave, and provides the result as image information.

In FIG. 1, an object S to be inspected is, for example, an electronic component, such as an integrated circuit, a large scale integrated circuit or the like. The object S to be inspected is sunk within a medium which transmits ultrasonic waves, for example a water tank filled with water. For some applications, a liquid other than water, for example oil, may be used. A probe 1 for performing transmission and reception of ultrasonic wave is mounted to a vertical moving unit 2 and a horizontal moving unit 3 with its front end immersed in the water. A pulser/receiver 4, which has the function of generating high-voltage pulses for transmitting ultrasonic wave and amplifying received signals, is connected to the probe 1. The amplified output from the pulser receiver 4 is connected to a surface-signal processing circuit 5 and an internal-signal processing circuit 6. The output from the surface-signal processing circuit 5 branches to three outputs. The first and second outputs are connected to a distance-in-water calculation circuit 9 via a maximum-value detection circuit 7 and a surface-reflection counting circuit 8, respectively. The third output is connected to an internal-reflection counting circuit 10 together with the output from the internal-signal processing circuit 6. The output from the internal-reflection counting circuit 10 is connected to a target-distance-in-water evaluation circuit 12 via a calculation circuit 11 which calculates the sonic velocity in an object to be inspected together with the output from the distance-in-water calculation circuit 9. The output from the target-distance-in-water evaluation circuit 12 is connected to a distance-in-water comparison circuit 13 together with the output from the distance-in-water calculation circuit 9. The output from the distance-in-water comparison circuit 13 is connected to the vertical moving unit 2 via a vertical-driving-signal generation circuit 14. Further provided are an apparatus-synchronizing-signal generator 15 and a timing-reference-signal generation circuit 16. The output from the generator 15 is connected to the pulser/receiver 4 and the surface-reflection counting circuit 8. The output from the generation circuit 16 is connected to the surface-reflection counting circuit 8 and the internal-reflection counting circuit 10.

Setting conditions, including a desired depth d for focus within the object to be inspected, the thickness $L_s$ of the object and the velocity of sound $V_w$ in water are input and set by the operator from a depth input unit 17, a thickness input unit 18 and a sonic-velocity-in-water input unit 19, respectively. The outputs from the depth input unit 17, the thickness input unit 18 and the sonic-velocity-in-water input unit 19 are connected to the target-distance-in-water evaluation circuit 12, the calculation circuit 11 of the sonic velocity in an object to be inspected, and the distance-in-water calculation circuit 9 and the target-distance-in-water evaluation circuit 12, respectively.

Furthermore, outputs from the horizontal moving unit 3 and a phase detection circuit 20 connected to the internal-signal processing circuit 6 are input to an image processing circuit 21, the output from which is connected to an image display unit 22, such as CRT or the like, and a printing unit 23, such as a printer or the like.

The operation of the present invention in the above-described configuration will now be explained.

In synchronization with the apparatus-synchronizing signal, which may be, for example, a clock signal, the pulser/receiver 4 generates high-voltage pulses which are applied to the probe 1. The probe 1 transmits an ultrasonic beam which is irradiated onto the object S to be inspected via water. Each ultrasonic echo as reflected by the surface, by the inner portion or by the base of the object S to be inspected is received again by the probe 1, amplified by the pulser receiver 4, and transmitted to the surface-signal processing circuit 5 and the internal-signal processing circuit 6. These two signal processing circuits 5 and 6 have time-gating and threshold-discriminating functions, and extract only a received signal exceeding a predetermined threshold value within a predetermined time gate based on the apparatus-synchronizing signal to extract the signal as a surface signal, an internal signal or a bottom signal, respectively. That is, the time required for the pulses to be reflected from the relevant portion of the object and returned is calculated and used to establish the time gate. The surface-reflection counting circuit 8 counts a timing reference signal, which is advantageously a sufficiently fine clock signal having a period $t_w$, between the apparatus-synchronizing signal and the surface signal, that is, a time difference, and outputs the result $N_w$. The distance-in-water calculation circuit 9 calculates the distance $L_w$ in water from the value $N_w$ obtained from the surface-reflection counting circuit 8, the input value $V_w$ from the sonic-velocity-in-water input unit 19, and the output from the timing-reference-signal generation circuit 16, that is, the time $t_w$ corresponding to one period of the timing reference signal according to the following formula.

$$L_w = N_w \times t_w \times V_w \times \tfrac{1}{2}.$$

The above-described operation is repeated while moving the probe 1 slightly in the vertical direction by the vertical moving unit 2. During this process, the maximum-value detection circuit 7 outputs a detection signal when it detects the maximum value of the amplitude of the surface signal. The amplitude of the surface signal has its maximum value when the ultrasonic beam is focused onto the surface of the object S to be inspected, and the distance in water when the detected maximum value signal is output is the measured focal length F in water of the probe 1.

On the other hand, the internal-reflection counting circuit 10 counts the timing reference signal between the surface signal and the internal signal or between the surface signal and the bottom signal, that is, the time difference, and outputs the corresponding result of counting $t_s$. The velocity of sound $V_s$ within the object S to be inspected is calculated from the result of counting $t_s$, the thickness $L_s$ of the object S to be inspected, which was input to the thickness input unit 18 and the input value $N_s$ of the depth from the surface of the object S to be inspected to an internal reflective source within the object S to be inspected. $V_s$ is calculated according to the following formula.

$$V_s = L_s / (N_s \times t_s \times \tfrac{1}{2}).$$

From the values of the focal length F in water of the probe 1, the sonic velocity $V_s$ of the object to be inspected and the desired depth d to be inspected obtained in the above-described process, the target distance $W_p$ in water is evaluated in the target-distance-in-water evaluation circuit 12 according to the following formula.

$$W_p = F - d \cdot V_s / V_w.$$

It is readily apparent that if one of the focal length or the sonic velocity of the object is known in advance from prior measurement or other sources, it is only necessary to determine the other.

The result is input to the distance-in-water comparison circuit 13, which compares the input target distance $W_p$ in water with the distance $L_w$ in water from the probe 1 to the object to be inspected at that moment, and outputs a differential signal which is proportional to the difference between the two distances. The differential signal is input to the vertical-driving-signal generation circuit 14, and is transmitted to the vertical moving unit 2 as a driving signal for driving the probe 1 in the direction to reduce the value of the differential signal. As a result, the distance in water gradually approaches the target distance $W_p$ in water, and finally, the focus of the ultrasonic beam exactly coincides with the desired depth d.

After the above-described focusing process has been completed, ultrasonic inspection of the object to be inspected is performed. Ultrasonic waves are emitted toward the object to be inspected while the probe 1 is being moved substantially two-dimensionally in horizontal directions over the object S to be inspected by the horizontal moving unit 3, and reflected signals of the ultrasonic waves reflected by the object to be inspected are received. The internal-reflection counting circuit 10, the internal-signal processing circuit 6 and the phase detection circuit 20 detect information about the depth, strength and phase relative to the received reflected signals. By providing time gate for the reflected signals, it is possible to take out only reflected signals from the desired depth within the object to be inspected, to detect an air layer (a detached layer) within the object to be inspected at the desired depth from the directions of the phases of the taken-out reflected signals from the desired depth, and to detect the degree of detachment of the detached layer from the strengths of the signals. More particularly, the obtained strengths have attached thereto positive or negative signs in accordance with the phases and are then provided as the detected data. By performing the detection two-dimensionally, an ultrasonic image visualized by image contrast or colors in accordance with the values of the detected data is formed by the image processing circuit 21, and the result is output to the image display unit 22 or the printing unit 23. The ultrasonic image of the object to be inspected at the desired depth can thus be obtained. A more detailed explanation relative to the above-described processing is provided, for example, in Japanese Patent Public Disclosure (Kokai) No. 63-47658 (1988).

As described above, according to the present invention in the first embodiment, since inspection is performed by automatically making the focus of a focusing-type ultrasonic probe coincide with a desired depth within an object to be inspected, the present invention has the advantages that troublesome human operation becomes unnecessary, misoperation decreases, and efficiency in inspection can be increased.

Suitable examples of inspection by the apparatus in the present embodiment are as follows.

Detection of cracks and voids within IC's in molded packages, and inspection of the adhesion state at the boundary between a chip and a lead frame.

Inspection of delamination in ceramic multilayer capacitors.

Soldering quality inspection of chip components on a high-density-mounted ceramic substrate.

Inspection of internal defects in new materials, composite materials and the like.

Next, a further improved second embodiment of the present invention will be explained.

Figure 2:
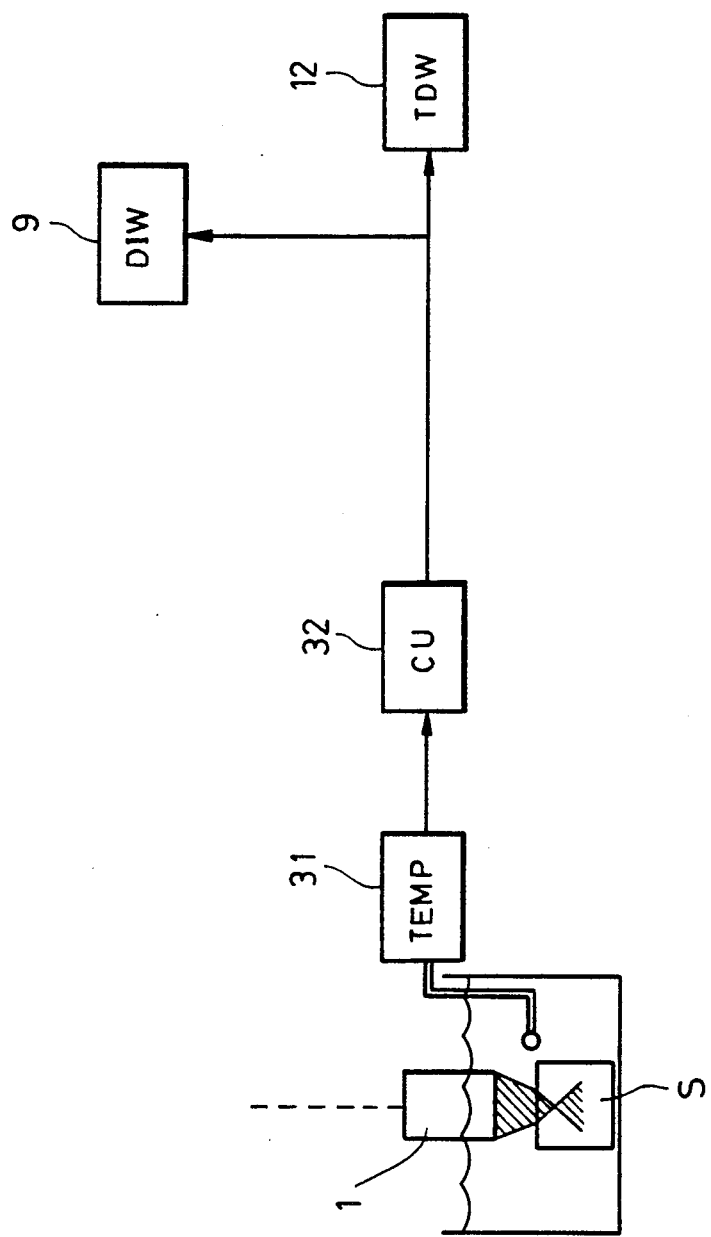
FIG. 2 is a partial configurational circuit diagram of a second embodiment of the present invention.

In the above-described first embodiment, there was adopted a method in which the operator inputs the velocity of sound in water. The velocity of sound in water which includes few impurities has the property of depending substantially only on temperature. FIG. 2 shows the partial configurational diagram of an ultrasonic apparatus of the second embodiment. In FIG. 2, the output from a water-temperature sensor 31 provided in water is input to a sonic-velocity-in-water conversion unit 32, the output from which is input to the distance-in-water calculation circuit 9 and the target-distance evaluation circuit 12.

In this configuration, the sonic-velocity-in-water conversion unit 32 obtains the velocity of sound $V_w$ in water by conversion, and this value is used in place of the input value used in the first embodiment.

Thus, according to the present embodiment, it is possible to omit the operation in which the operator inputs the velocity of sound $V_w$ in water.

Although the embodiments described above have been applied to ultrasonic inspection apparatuses which are suitable for inspection of electronic components, objects to be inspected may be other than electronic components. Furthermore, the present invention is not limited to ultrasonic inspection apparatuses, but may also be widely used as an autofocusing mechanism for various apparatuses utilizing ultrasonic wave, for example, ultrasonic heating therapeutic apparatuses, ultrasonic calculus-breaking apparatuses and the like in the medical field.

What is claimed is:

1. An ultrasonic apparatus comprising:
   irradiating means including an ultrasonic probe for irradiating a focused ultrasonic beam onto an object;
   reception means for receiving ultrasonic waves reflected from the object;
   setting means for setting a desired depth to a predetermined point within the object;
   detecting means for detecting at least either one of an inherent focal length of said irradiating means and a velocity of sound within said object;
   evaluation means for evaluating a distance between said probe and said object at which a focus of said irradiating means coincides with the depth to the predetermined point within the object in accordance with a result of said detecting means; and
   driving means for adjusting a distance between said probe and said object so as to make the adjusted distance coincide with an evaluated distance of said evaluation means.

2. An ultrasonic apparatus according to claim 1, wherein said object to be inspected is placed within a medium which transmits ultrasonic waves.

3. An ultrasonic apparatus according to claim 2, wherein said medium comprises water.

4. An ultrasonic apparatus according to claim 3 further comprising:
   means for setting a thickness of the object to be inspected;
   means for detecting temperature in the water in which said object to be inspected is placed; and
   means for calculating a velocity of sound in water from the detected water temperature.

5. An ultrasonic apparatus according to claim 3, wherein said apparatus comprises means for setting a thickness of the object to be inspected and means for setting a velocity of sound in water.

6. An ultrasonic apparatus according to claim 5, wherein said detection means detects as the inherent focal length F of said probe a distance in water between the probe and the object to be inspected at which a maximum reflected signal is obtained when an ultrasonic beam is irradiated onto the object to be inspected while said probe is being moved in a vertical direction.

7. An ultrasonic apparatus according to claim 6, wherein said distance in water is evaluated from a time difference from the moment when the ultrasonic beam is irradiated to the moment when reflected waves are received, and from the velocity of sound in water.

8. An ultrasonic apparatus according to claim 5, wherein said detection means detects the velocity of sound within said object to be inspected from a measured time difference and a physical dimension of said object to be inspected, said measured time difference being a selected one of a time difference between a signal reflected from a surface of said object and a signal reflected from a bottom of said object and a time difference between the surface-reflected signal and a signal reflected from a reflective source within said object, and said physical dimension being a correspondingly selected one of the thickness of said object and a depth at which said reflective source is positioned within said object.

9. An ultrasonic apparatus according to claim 5, wherein said evaluation means evaluates the distance between said probe and said object to be inspected at which the focus of said probe coincides with said desired depth from a focal length in water of the probe, a velocity of sound within the object to be inspected, the velocity of sound in water and the desired depth.

10. An ultrasonic inspecting apparatus comprising:
   irradiating means including an ultrasonic probe for irradiating a focused ultrasonic beam onto an object to be inspected;
   reception means for receiving ultrasonic waves reflected from the object to be inspected;

setting means for setting a desired depth to a predetermined plane within the object to be inspected;

detection means for detecting at least either one of an inherent focal length of said irradiating means and a velocity of sound within said object to be inspected;

evaluation means for evaluating a distance between said irradiating means and said object to be inspected at which a focus of said irradiating means coincides with the depth to the predetermined plane within the object to be inspected in accordance with a result of said detecting means;

first driving means for adjusting a distance between said irradiating means and said object to be inspected so as to make the adjusted distance coincide with an evaluated distance of said evaluation means;

second driving means for moving said irradiating means relative to the object to be inspected substantially parallel to said predetermined plane; and forming means for forming an ultrasonic image of said desired depth within the object to be inspected from a result of said reception means.

11. An ultrasonic apparatus according to claim 10, wherein said object to be inspected is placed within a medium which transmits ultrasonic waves.

12. An ultrasonic apparatus according to claim 10, wherein a defect within said object to be inspected is discriminated in accordance with the direction of a phase of a signal obtained by said reception means and said ultrasonic image discriminating a defect is formed.

13. An ultrasonic apparatus according to claim 10, wherein said object to be inspected comprises an electronic component.

14. An ultrasonic apparatus according to claim 10, wherein said apparatus comprises means for obtaining a signal reflected from the desired depth within the object to be inspected by providing a time gate to the received ultrasonic waves.

15. An ultrasonic apparatus according to claim 12, further comprising:
means for detecting a phase and a strength of a reflected ultrasonic wave signal, and
wherein said discrimination means discriminates a state within the object to be inspected from the detected phase and strength.

16. An ultrasonic apparatus according to claim 15 wherein said reflected ultrasonic wave phase and strength detecting means detects the strength of said reflected signal and attaches a positive or negative sign in accordance with the phase of said reflected signal to provide a measured value.

17. An ultrasonic inspecting apparatus for inspecting a defect within an object comprising:
irradiating means including an ultrasonic probe for irradiating a focused ultrasonic beam onto an object to be inspected;
reception means for receiving ultrasonic waves reflected from the object to be inspected;
setting means for setting a desired depth to a predetermined plane within the object to be inspected;
evaluation means for evaluating a distance between said probe and said object to be inspected at which a focus of said irradiating means coincides with the depth to the predetermined plane within the object to be inspected;

first driving means for adjusting a distance between said probe and said object to be inspected so as to make the adjusted distance coincide with an evaluated distance of said evaluation means;

second driving means for moving said probe relative to the object to be inspected substantially parallel to said predetermined plane; and forming means for forming an ultrasonic image discriminating a defect of said desired depth within the object to be inspected from a result of said reception means.

18. An ultrasonic inspecting apparatus according to claim 10, wherein said second driving means moves two-dimensionally and forms a two-dimensional ultrasonic image.

19. An ultrasonic inspecting apparatus according to claim 18, wherein said forming means comprises an output device for outputting the ultrasonic image.

20. An ultrasonic inspecting apparatus according to claim 17, wherein said object to be inspected is placed within a medium which transmits ultrasonic waves.

21. An ultrasonic inspecting apparatus for inspecting a defect within an object according to claim 17, wherein the defect is discriminated in accordance with the direction of a phase of said received ultrasonic waves.

22. An ultrasonic inspecting apparatus according to claim 17, wherein said object to be inspected comprises an electronic component.

23. An ultrasonic inspecting apparatus according to claim 17, wherein said apparatus comprises means for obtaining a signal reflected from the desired depth within the object to be inspected by providing a time gate to the received ultrasonic waves.

24. An ultrasonic inspecting apparatus according to claim 17, further comprising means for detecting a phase and a strength of a reflected ultrasonic wave signal, and wherein said forming means discriminates a state within the object to be inspected from the detected phase and strength.

25. An ultrasonic inspecting apparatus according to claim 24, wherein said reflected ultrasonic wave phase and strength detecting means detects the strength of said reflected signal and attaches a positive or negative sign in accordance with the phase of said reflected signal to provide a measured value.

26. An ultrasonic inspecting apparatus according to claim 17, wherein said second driving means moves two-dimensionally and said forming means forms a two-dimensional ultrasonic image.

27. An ultrasonic inspecting apparatus according to claim 26, wherein said forming means comprises an output device for outputting the ultrasonic image.

28. A method for inspecting a defect within an object using ultrasonic waves comprising:
irradiating a focused ultrasonic beam from an ultrasonic probe onto an object to be inspected;
receiving ultrasonic waves reflected from the object to be inspected and outputting received signals;
setting a desired depth to a predetermined plane within the object to be inspected;
evaluating a distance between said probe and said object to be inspected at which a focus of said probe coincides with the depth to the predetermined plane within the object to be inspected;
adjusting distance automatically between said probe and said object to be inspected so as to make the adjusted distance coincide with said evaluated distance;

moving said probe relative to the object to be inspected substantially parallel to the predetermined plane; and forming an ultrasonic image discriminating the defect of said desired depth within the object to be inspected from said received signals.

29. A method for inspecting a defect according to claim 28, wherein the defect is discriminated in accordance with the direction of a phase of said received signals.

30. A method for inspecting a defect according to claim 28, wherein said object to be inspected comprises an electric component.

* * * * *

UNITED STATES PATENT AND TRADEMARK OFFICE
CERTIFICATE OF CORRECTION

PATENT NO. : 5,301,552
DATED : April 12, 1994
INVENTOR(S) : MASATO NAGURA ET AL.

It is certified that error appears in the above-identified patent and that said Letters Patent is hereby corrected as shown below:

COLUMN 5

Line 18, "follows." should read --follows:--.

COLUMN 7

Line 48, "claim 15" should read --claim 15,--.

Signed and Sealed this

Twentieth Day of December, 1994

Attest:

BRUCE LEHMAN

Attesting Officer　　　Commissioner of Patents and Trademarks